(12) United States Patent
Bahado-Singh et al.

(10) Patent No.: US 10,835,148 B2
(45) Date of Patent: Nov. 17, 2020

(54) METABOLOMIC PREDICTION OF CONGENITAL HEART DEFECT DURING PREGNANCY, NEWBORN AND PEDIATRIC STAGES

(71) Applicant: BIOSCREENING AND DIAGNOSTICS LLC, Detroit, MI (US)

(72) Inventors: Ray O. Bahado-Singh, Gross Pointe Shores, MI (US); Kypros Nicolaides, London (GB)

(73) Assignee: Bioscreening & Diagnostics LLC, Detroit, MI (US)

( * ) Notice: Subject to any disclaimer, the term of this patent is extended or adjusted under 35 U.S.C. 154(b) by 17 days.

(21) Appl. No.: 15/039,121

(22) PCT Filed: Nov. 25, 2014

(86) PCT No.: PCT/US2014/067414
§ 371 (c)(1),
(2) Date: May 25, 2016

(87) PCT Pub. No.: WO2015/081100
PCT Pub. Date: Jun. 4, 2015

(65) Prior Publication Data
US 2017/0156627 A1    Jun. 8, 2017

Related U.S. Application Data

(60) Provisional application No. 61/908,985, filed on Nov. 26, 2013, provisional application No. 61/909,006, filed on Nov. 26, 2013.

(51) Int. Cl.
*G01N 33/00*    (2006.01)
*A61B 5/055*    (2006.01)
(Continued)

(52) U.S. Cl.
CPC ............ *A61B 5/055* (2013.01); *A61B 5/4343* (2013.01); *A61B 8/0866* (2013.01);
(Continued)

(58) Field of Classification Search
CPC .......................... A61B 5/055; G01N 33/6893
(Continued)

(56) References Cited

U.S. PATENT DOCUMENTS

2013/0295679 A1    11/2013    Kenny et al.

FOREIGN PATENT DOCUMENTS

| CA | 2445101 | 10/2002 |
| WO | WO2005036198 | 4/2005 |
| WO | WO2011087760 | 7/2011 |

OTHER PUBLICATIONS

Bahado-Singh RO, Akolekar R, Chelliah A, et al. Metabolomic analysis for first-trimester trisomy 18 detection. Am J Obstet Gynecol 2013;209:65.e1-9. (Year: 2013).*

(Continued)

*Primary Examiner* — Christopher Adam Hixson
*Assistant Examiner* — Emily R. Berkeley
(74) *Attorney, Agent, or Firm* — Lee & Hayes, P.C.

(57) ABSTRACT

Particular aspects of the invention are methods for assaying metabolite levels in samples from a patient during pregnancy using nuclear magnetic resonance and direct flow injection mass spectrometry. In various methods, the assayed metabolites may be acylcarnitine or one or more of C3-OH (hydroxypropionylcarnitine), C5-OH (C3DC), C10, C5:1-DC (glutaconylcarnitine), C14:1-OH (hydroxytetradecenoylcarnitine) and C14:2-OH. One or more methods also may include measuring nuchal translucency of the fetus. Other methods relate to predicting fetal congenital heart defects in a fetus.

15 Claims, 5 Drawing Sheets

(51) Int. Cl.
   A61B 5/00      (2006.01)
   G01N 33/68     (2006.01)
   G01R 33/465    (2006.01)
   A61B 8/08      (2006.01)
   G01R 33/46     (2006.01)
(52) U.S. Cl.
   CPC ....... *G01N 33/6893* (2013.01); *G01R 33/465* (2013.01); *A61B 2503/045* (2013.01); *G01N 2560/00* (2013.01); *G01N 2800/32* (2013.01); *G01N 2800/385* (2013.01); *G01R 33/4625* (2013.01)
(58) Field of Classification Search
   USPC .......................................................... 436/86
   See application file for complete search history.

(56) References Cited

OTHER PUBLICATIONS

Jegatheeswaran et al. "Costs of Prenatal Detection of Congenital Heart Disease" Am J Cardiol 2011;108:1808-1814 (Year: 2011).*
Psychogios N, Hau DD, Peng J, Guo AC, Mandal R, et al. (2011) The Human Serum Metabolome. PLoS ONE 6(2): e16957. (Year: 2011).*
Hobbs et al. Am J Clin Nutr 2005;82:598-604 (Year: 2005).*
Horgan et al. J. Proteome Res. 2011, 10, 3660-3673 (Year: 2011).*
Human Metabolome Database (HMDB) - metabocard for L-Acetylcarnitine (http://www.hmdb.ca/metabolites/HMDB0000201) created Nov. 16, 2016 and accessed by examiner on Nov. 7, 2018 (Year: 2016).*
Bahado-Singh, "Metabolomic predicition of fetal congenital heart defect in the first trimester", Sep. 2014, Amercian Journal of Obstetrics & Gynecology, vol. 211, No. 3, pp. 240.e11-240.e14.
Bouatra, "The Human Urine Metabolome", Sep. 2013, PLOS ONE, vol. 8, No. 9, 28 pages.
The Extended European Search Report dated Sep. 6, 2017 for European patent application No. 14865429.6, 10 pages.
Mandal, et al., "Multi-platform characterization of the human cerebrospinal fluid metabolome: a comprehesnive and quantitative update", Apr. 30, 2012, Genome Medicine, vol. 4, No. 38, 12 pages.
Castelnovi, et al., "Maternal isovaleric acidemia: Observation of distinctive changes in plasma amino acids and 1 I 1 I carnitine profiles during pregnancy", retrieved on Jan. 15, 2015 at <<http://www.sciencedirect.com/science/article/pii/S0009898110005206><doi:10.1016/j.cca.2010.08.023>>, vol. 411, No. 23-24, Dec. 2010, pp. 2101-2103.
Lehmann, et al., "Medium Chain Acylcarnitines Dominate the Metabolite Pattern in Humans uder Moderate Intensity Excercise and Support Lipid Oxidation", retrieved on Jan. 15, 2015 at <<http://www.ncbi.nlm.nih.gov/pmc/articles/PMC2902511/pdf/pone.0011519.pdf><doi:10.1371/journal.pone.0011519>>, PLoS One, vol. 5, No. 7, e11519, Jul. 2010, pp. 1-12.
PCT Search Report and Written Opinion dated Feb. 9, 2015 for PCT Application No. PCT/US14/67414, 13 pages.
Solberg, et al., "Metabolomic Analyses of Plasma Reveals New Insights into Asphyxia arid Resuscitation in Pigs", retrieved on Jan. 15, 2015 at <<URL:http://www.plosone.org/article/fetchSingleRepresentation.action?uri=info:doi/10.1371/journal.pone.0009606><URL:http://www.plosone.org/article/fetchSingleRepresentation.action?uri=info:doi/10.1371/journal.pone.0009606.s001><doi:10.1371/journal.pone.0009606><doi:10.1371/journal.pone.0009606.s001>>, PLoS One, vol. 5, No. 3, e9606, Mar. 2010, pp. 1-12.
European Office Action dated Jun. 8, 2020 for European Patent Application No. 14865429.6, a counterpart foreign application of the U.S. Appl. No. 15/039,121, 5 pages.

* cited by examiner

METABOLOMIC PREDICTION OF CONGENITAL HEART DEFECT DURING PREGNANCY, NEWBORN AND PEDIATRIC STAGES

CROSS REFERENCE TO RELATED APPLICATIONS

The present application is a U.S. National Phase Application of International Application No. PCT/US2014/67414, filed Nov. 25, 2014, which claims the benefit of U.S. Provisional Application No. 61/908,985, filed Nov. 26, 2013, and U.S. Provisional Application No. 61/909,006, filed Nov. 26, 2013, all of which are hereby incorporated by reference in their entirety.

TECHNICAL FIELD OF INVENTION

The present invention relates to the identification and use of metabolomic markers in maternal, newborn or pediatric serum for the prediction or diagnosis of congenital heart defects (CHD).

BACKGROUND

Congenital heart defect (CHD) is the most important category of congenital anomalies based both on its frequency, 0.6 to 0.8% of all the births, and cumulative health care costs. In contrast to the routine population pregnancy screening for the detection of less common fetal anomalies such as aneuploidies and neural tube defect, there is no similar screening policies for CHD.

Reliable detection of CHD is the "holy grail" of prenatal screening. This directly reflects the importance of CHD. Congenital anomaly is the most important cause of infant death in the USA. The prenatal diagnosis of CHD has distinct advantages including the opportunity for early counseling of families-facilitating reproductive choices. Decisions such as transferring of care to an appropriate pregnancy specialist within the same institution or complete transfer to another institution with the appropriate high risk obstetrical, newborn and pediatric expertise often need to be made. Given the high rate of intervention and hospitalization in CHD cases there are significant social and financial implications to affected families. Prenatal diagnosis of CHD has been reported to improve medical costs. Data from the USA also found a greater than tenfold increase in average newborn transportation costs when CHD was diagnosed postnatally compared to prenatal detection. Finally, in some categories of CHD prenatal diagnosis reportedly may improve overall outcome compared to those in which the diagnosis is made after birth.

There is suggestive evidence that at least in some types of CHD, prenatal diagnosis may improve newborn outcome. The increasing interest in fetal cardiac intervention for such lesions as aortic stenosis and hypoplastic left heart syndrome creates another potentially powerful argument in favor of prenatal diagnosis, at least for cardiac anomalies that are amendable to such approaches.

An area of concern with respect to the prenatal diagnosis of any congenital anomalies has been concerns about medical selection against affected fetuses. Data from France have however shown that pregnancy termination rates have not increased in proportion to improving prenatal diagnosis of CHD. Indeed termination rates have leveled off and pregnancy termination was exceptional among the more common categories of CHD while at the same time there has been a reduction in early neonatal deaths.

Ultrasound remains the most widely used prenatal tool for the detection of fetal CHD. While specialist centers that care for high risk patients report high sensitivities for CHD detection the overall performance of prenatal ultrasound in the general population remains substantially below that required for an effective screening test. A recent study in the USA found that slightly less than 40% of CHD cases were detected prenatally in a state-wide obstetric population that had an ultrasound exam at the appropriate gestational age. The overall accuracy of prenatal ultrasound is significantly constrained by its dependence on operator expertise, equipment quality and uncontrollable variables such as fetal position and maternal obesity. The difficulties associated with the of diagnosis of CHD is moreover not limited to the prenatal period as a relatively high percentage of critical CHD fail to be diagnosed in newborns prior to discharge home.

Metabolomics is a branch of the "omics" sciences in which high through-put techniques are used for the identification and quantification of the small molecules that constitute the metabolome. Metabolites are a very diverse group of molecules including but not limited to amino acids, nucleic acids, lipids, peptides, sugars and organic acids. They represent the substrates and byproducts of the various enzymatic reactions within the cells but also respond to and reflect various physiologic influences, e.g. age and gender, moreover pathologic and environmental influences including, diet, toxins, pharmacologic agents and stress which are important causes and modifiers of disease, significantly influence the metabolome. Based on the latter, metabolomics appears to give a more complete description of cellular phenotype than the genome, transcription or proteome.

Increasingly metabolomics is being used to develop biomarkers for the detection, screening and monitoring of complex diseases. There is limited prior evidence that CHD may either be caused by or associated with metabolic disturbance in humans. Abnormalities of folate and single carbon metabolism have been linked to the development of CHD. Comprehensive metabolomic analysis for the prediction of fetal, newborn or pediatric CHD has not been previously reported.

SUMMARY

Prenatal ultrasound remains the only tool currently available for the detection of CHD. Studies that are primarily from referral specialist centers report high diagnostic accuracy with specialized echocardiographic techniques such as Spatio-Temporal Imagery Correlation (STIC) and combined cardiac anomaly detection. Most population studies however paint a considerable less optimistic view of achievable detection rates even among groups with high, i.e. greater than 90% exposure to prenatal ultrasound. The majority, close to 80% of non-chromosomal CHD cases, failed to be diagnosed prenatally in 29 population-based registries in 16 European countries.

The estimated current screening practices in developed countries detected only 30-50% of fetal CHD cases. Despite the widely reported low CHD screening performance, few studies have however examined the reasons for such low diagnosis rates. One study systematically reviewed the causes of low CHD detection rate in a 10 year review of a statewide surveillance program in Utah, USA. (Pinto N M, Keenan H T, Minich L L, Puchalksi M D, Heywood M, Botto L D. Barriers to prenatal detection of congenital heart disease: a population based study. Ultrasound Obstet Gynecol 2012; 40:418-25.) CHD prenatal detection rate was only 39% overall. The main factors accounting for failure to diagnose CHD prenatally were location in which the exam was performed, i.e. hospital versus high risk maternal fetal medicine office, the ultrasound interpreter i.e. obstetrician, radiologist or maternal fetal medicine specialist and the absence or presence of extracardiac anomalies. A family history of CUD also increased the detection of cardiac anomalies, likely due to the identification of the patient as being at elevated risk with greater attention to detail on the ultrasound exam. Despite enhanced chances of diagnosis when an MFM performed the ultrasound, in 25% of such cases scanned MFM offices the diagnosis was missed. There was universal availability of ultrasound in the study population. Other factors such as gestational age at the performance of ultrasound, maternal body habitus and fetal lie are known to affect the chances of detecting a fetal cardiac anomaly. None of these limitations would appear to be relevant or significant with maternal biomarkers such as the examples claimed in the present invention.

The inventors have discovered significant disturbance in lipid including phosphatidyl-choline and various sphingolipids and choline metabolism in the serum of women carrying CHD fetuses. The present invention relates to the identification and use of metabolomic markers in maternal, newborn or pediatric serum for the prediction and diagnosis of congenital heart defects (CHD).

In one embodiment, the invention provides a method for assaying metabolite levels in a biologic sample from a patient during pregnancy using nuclear magnetic resonance and mass spectrometry. In some embodiments, the assay is performed during the first trimester of pregnancy. In some embodiments, the assay is performed during the second trimester of pregnancy. In some embodiments, the assay is performed during the third trimester of pregnancy. In some embodiments, the biologic sample is a maternal bodily fluid such as saliva, urine, amniotic fluid, breath condensate, blood or placental tissue. In some embodiments, the biologic sample is blood.

In some embodiments, the metabolite is an acylcarnitine. In some embodiments, the metabolite is one or more of C3-OH (hydroxypropionylcarnitine), C5.OH (C3DC), C10, C5:1-DC (glutaconylcarnitine), C14:1-OH (hydroxytetradecenoylcarnitine) and C14:2-OH.

In one embodiment, the invention further provides measuring the nuchal translucency of the fetus by ultrasound.

In one embodiment, the invention provides a method for predicting congenital heart defects in a fetus, comprising measuring metabolite levels in a biologic sample from the mother using nuclear magnetic resonance and direct flow injection mass spectrometry. In some embodiments, the measuring is performed during the first trimester of pregnancy. In some embodiments, the assay is performed during the second trimester of pregnancy. In some embodiments, the assay is performed during the third trimester of pregnancy. In some embodiments, the biologic sample is a maternal bodily fluid such as saliva, urine, amniotic fluid, breath condensate or blood. In some embodiments, the biologic sample is blood.

In some embodiments, the metabolite is an acylcarnitine. In some embodiments, the metabolite is one or more of C3-OH (hydroxypropionylcarnitine), C5.OH (C3DC), C10, C5:1-DC (glutaconylcarnitine), C14:1-OH (hydroxytetradecenoylcarnitine) and C14:2-OH.

In one embodiment, the invention further provides measuring the nuchal translucency of the fetus by ultrasound.

In one embodiment, the invention further provides counseling the mother. In some embodiments, counseling comprises recommending transfer of care to a facility specializing in high-risk pregnancies. In some embodiments, counseling comprises recommending transfer of care to a physician specializing in high-risk pregnancies.

In one embodiment, the invention provides method for predicting congenital heart defects in a fetus or embryo, comprising measuring metabolite levels in a biologic sample from the mother, wherein the metabolites are more than one of C3-OH (hydroxypropionylcarnitine), C5.OH (C3DC), C10, C5:1-DC (glutaconylcarnitine), C14:1-OH (hydroxytetradecenoylcarnitine) and C14:2-OH. In some embodiments, the metabolites are C3-OH (hydroxypropionylcarnitine), C5:1-DC (glutaconylcarnitine), and (hydroxytetradecenoylcarnitine). In some embodiments, measuring is achieved by nuclear magnetic resonance and direct flow injection mass spectrometry.

In one embodiment, mRNA microchip (RT-PCR) analysis is used to measure the expression levels of CHD related genes.

In one embodiment, the invention provides a method for assaying metabolite levels in a biologic sample from a patient using nuclear magnetic resonance and mass spectrometry. In one embodiment, the patient is a newborn. In one embodiment, the patient is a pediatric patient. In one embodiment, the patient is an embryo i.e. <8 weeks gestational age.

In one embodiment, the metabolite is an acylcarnitine. In one embodiment, the metabolite is one or more of C3-OH (hydroxypropionylcarnitine), C5.OH (C3DC), C10, C5:1-DC (glutaconylcarnitine), C14:1-OH (hydroxytetradecenoylcarnitine) and C14:2-OH.

In one embodiment, the biologic sample is a bodily fluid selected from the group consisting of saliva, urine, breath condensate or blood. In one embodiment, the biologic sample is blood. In one embodiment, the sample is placenta.

In one embodiment, the invention provides a method for diagnosing congenital heart defects in a patient, comprising measuring metabolite levels in a biologic sample using nuclear magnetic resonance and mass spectrometry. In one embodiment, the patient is a newborn. In one embodiment, the patient is a fetus. In one embodiment, the patient is a pediatric patient.

In one embodiment, the metabolite is an acylcarnitine. In one embodiment, the metabolite is one or more of C3-OH (hydroxypropionylcarnitine), C5.OH (C3DC), C10, C5:1-DC (glutaconylcarnitine), C14:1-OH (hydroxytetradecenoylcarnitine) and C14:2-OH.

In one embodiment, the biologic sample is a bodily fluid selected from the group consisting of saliva, urine, breath condensate or blood, including umbilical cord blood. In one embodiment, the biologic sample is blood.

In one embodiment, the invention provides a method for diagnosing congenital heart defects in a newborn or pediatric patient, comprising measuring metabolite levels in a biologic sample, wherein the metabolites are more than one of C3-OH (hydroxypropionylcarnitine), C5.OH (C3DC), C10, C5:1-DC (glutaconylcarnitine), C14:1-OH (hydroxytetradecenoylcarnitine) and C14:2-OH. In one embodiment, the metabolites are C3-OH (hydroxypropionylcarnitine), C5:1-DC (glutaconylcarnitine), and (hydroxytetradecenoylcarnitine).

In one embodiment, measuring is achieved by nuclear magnetic resonance and direct flow injection mass spectrometry.

DETAILED DESCRIPTION

Definitions

Figure 1:
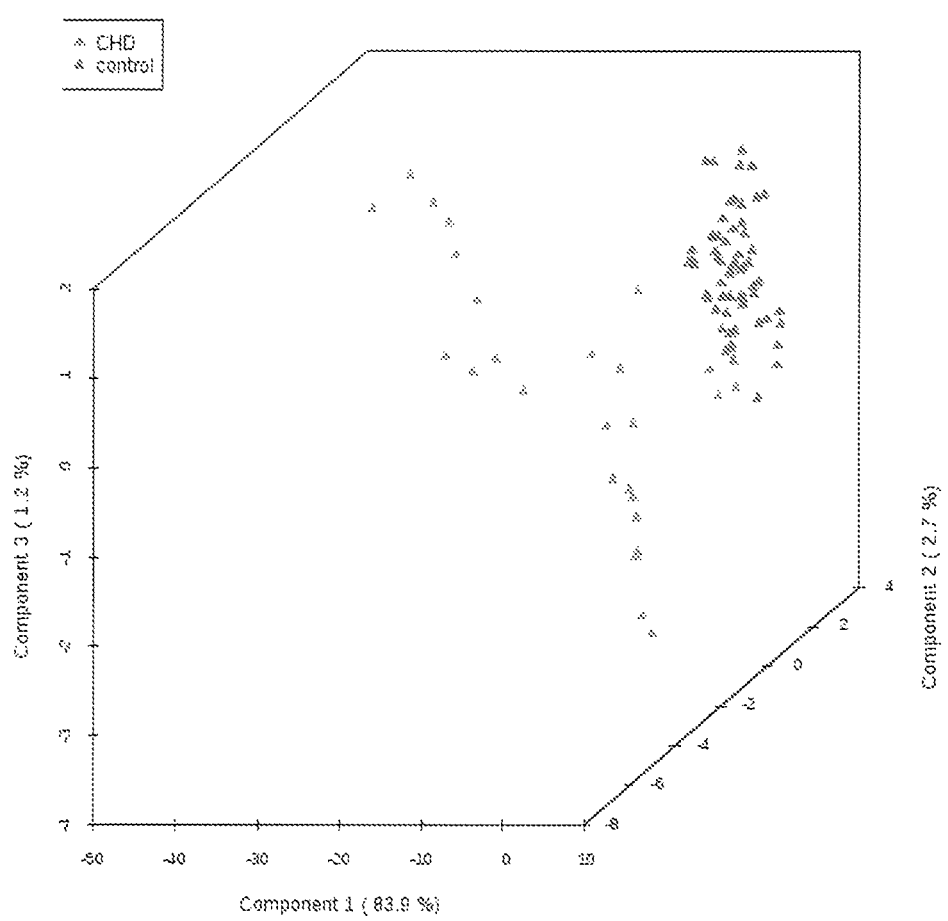
FIG. 1 depicts a 3-D PLS-DA plot based on DI-MS only.

As used herein, "nuclear magnetic resonance" or "NMR" refers to the absorption of electromagnetic radiation of a specific frequency by an atomic nucleus containing hydrogen ($H^+$) or a proton that is placed in a strong magnetic field, used especially in spectroscopic studies of molecular structure and in medicine to identify and measure molecules involved in metabolism.

As used herein, "direct flow injection mass spectrometry" or "DI-MS" refers to an analytic technique by which chemical substances are identified by sorting gaseous ions by mass using electric and magnetic fields, wherein sample introduction is by direct insertion with a probe or plate.

As used herein, "nuchal translucency" or "NT" refers to the measurement of the size of the subcutaneous translucent space behind the neck of the fetus using ultrasound at between 10 and 14 weeks of pregnancy, reflecting the amount of fluid that has accumulated under the skin of the fetus. Nuchal translucency is commonly used as a predictor of chromosome disorders such as, trisomy 18, Turner syndrome and Down syndrome.

The term "patient," as used herein, means an animal, preferably a human.

In the first such report the present invention demonstrates the feasibility of use of biomarkers for the prediction of CHD. Abnormal lipid metabolism appears to be a significant feature of CHD pregnancies.

While abnormality in metabolite levels in the folate pathway such as homocysteine and metabolites related to oxidative stress have been previously reported our study represents the first comprehensive untargeted metabolomics study for the prenatal prediction of CHD. The serum metabolomics profile of a first trimester pregnant women carrying CHD fetus in this study found significant elevation of acylcarnitines. Carnitine (β-hydroxy-γ-trimethylammonium butyrate) is a substance that plays a key role in the transfer of fatty acids into the mitochondria for metabolism and energy release. Long chain (multiple carbons) fatty acids bind with carnitine to form acylcarnitines which are transported into the mitochondria for sequential shortening which occurs two carbons at a time. This process is associated with the generation of potential energy stored in ATP. During periods of starvation these fatty acids constitute the main source of energy for skeletal muscle. Approximately 70% of myocardial energy is provided by mitochondrial fatty acid oxidation as described above.

Abnormality of folate metabolism has been linked to CHD in human and animal studies. Choline is an important nutrient that plays a role in lipid metabolism and in the formation of phosphotidyl choline for cell membrane synthesis. The two major roles of choline are for phospolipid synthesis and to serve as a methyl donor. Choline is oxidized to betaine in the mitochondria and betaine serves as an actual methyl donor which converts homocysteine to methionine. Increased levels of methionine are repeatedly associated with reduced risk of CHD while elevated homocysteine (a metabolic result of decreased methionine) is associated with increased CHD risk. Choline deficiency is also associated with increased lipid accumulation in the liver. There is thus a link between lipid metabolism and single carbon metabolism. Of note, in our data set there was a reduction in carnitine levels in CHD versus normal pregnancies. Providing further potential evidence of a metabolic disturbance in this pathway.

Disturbances of phosphatidyl choline metabolism is a prominent feature of several cancers including breast cancer. Cancer is a disorder characterized by rapid cell growth, division and apoptosis. Given the critical role of phosphotidylcholine in cell membranes, disturbance in choline metabolism would therefore appear understandable. Organogenesis in the embryonic period has obvious similarities to cancer. It is therefore possible that in CHD abnormalities of tissue re-modeling which affect the rate of cell membrane synthesis and destruction may be manifesting as abnormality of the choline and phosphotidylcholine metabolism.

Overall, we identified evidence of extensive phosphatidyl-choline and lipid abnormalities in the first trimester serum of pregnant women with CHD fetuses. Some of these metabolic abnormalities such as disturbance of carnitine levels and therefore lipid synthesis could plausibly be tied to aberrations of single carbon metabolism through choline. There is already extensive evidence of an association with altered homocysteine and methionine levels and the development of CHD, while the association with fetal CHD is new.

NMR Metabolomic Analysis

Prior publications have extensively described the use of the nuclear magnetic resonance (NMR) platform for metabolomic analysis of the serum. (Bahado-Singh R O, et al. Metabolomics and first-trimester prediction of early-onset preeclampsia. J Matern Fetal Neonatal Med 2012; 10:1840-7; Bahado-Singh R O, et al. Metabolomic analysis for first-trimester Down Syndrome Prediction. Am J Obstet Gyencol 2013; 208; 371.e1-8.) In brief the Varian Inova 500 MHz NMR spectrometer was used (International Equipment Treating limited, Vernon Hills, Ill.). Serum samples were filtered through 3-kd cut off centrifuge filter units (Amicon Micoron YM-3; Sigma-Aldrich, St. Louis, Mo.) to remove blood proteins. Three hundred and fifty microliters of samples was put into the centrifuge filter device and spun (10,000 rpm for 20 minutes) in order to remove macro molecules such as protein and lipoproteins. If the total volume of sample was <300 µl a 50-mmol $NaH_2PO_4$ buffer (pH7) was added to reach a total sample volume of 300 µl. Metabolite concentrations were adjusted for the dilution due to the buffer. Thereafter, 35 µl of $D_2O$ and 15 µl of buffer solution (11.667 mmol disodium-2,2-dimethyl-2-silceptentane-5-sulphonate, 730 mmol imidazole and 0.47% $NaN_3$ in $H_2O$) was added to the sample.

A total of 350 µl of sample was transferred to a micro cell NMR tube (Shigemi, Inc., Allison Park, Pa.). $^1$H-NMR spectra were collected on a 500-MHz Inova (Varian Inc, Palo Alto, Calif.) spectrometer with a 5-mm ITCN Z-gradient PFG cold-probe. The singlet produced by the disodium-2,2-dimethyel-2-silcepentane-5-sulphonate methyl groups was used as an internal standard by which to measure the chemical shift. The standard reference substance was set at 0 ppm and used for quantification of metabolites of interest. The $^1$H-NMR spectra were analyzed with a Chenomx NMR Suite Professional Software package (Version 7.1:Chenomx Inc. Edmonton, Alberta, Canada). This permits quantitative and qualitative analysis of the NMR spectrum observed. The observed NMR spectrum was manually fitted to an internal database. Each spectrum was evaluated by at least 2 NMR spectroscopists to minimize errors of quantitation and identification. Analysis of the metabolomics data was performed with the MetaboAnalyst web based statistical package.

Combined Direct Flow Injection and LC-MS/MS Compound Identification and Quantification We applied a targeted quantitative metabolomics approach to analyze the serum samples using a combination of direct injection mass spectrometry (AbsoluteIDQ™ Kit) with a reverse-phase LC-MS/MS Kit. The Kit is a commercially available assay from BIOCRATES Life Sciences AG (Austria). This kit, in combination with an ABI 4000 Q-Trap (Applied Biosystems/MDS Sciex) mass spectrometer, can be used for the targeted identification and quantification of up to 180 different endogenous metabolites including amino acids, acylcarnitines, biogenic amines, glycerophospholipids, sphingolipids and sugars. The method used combines the derivatization and extraction of analytes, and the selective mass-spectrometric detection using multiple reaction monitoring (MRM) pairs. Isotope-labeled internal standards and other internal standards are integrated in Kit plate filter for metabolite quantification. The AbsoluteIDQ kit contains a 96 deep-well plate with a filter plate attached with sealing tape, and reagents and solvents used to prepare the plate assay. First 14 wells in the Kit were used for one blank, three zero samples, seven standards and three quality control samples provided with each Kit. All the serum samples were analyzed with the AbsoluteIDQ kit using the protocol described in the AbsoluteIDQ user manual. Briefly, serum samples were thawed on ice and were vortexed and centrifuged at 13,000×g. 10 µL of each serum sample was loaded onto the center of the filter on the upper 96-well kit plate and dried in a stream of nitrogen. Subsequently, 20 µL of a 5% solution of phenyl-isothiocyanate was added for derivatization. After incubation, the filter spots were dried again using an evaporator. Extraction of the metabolites was then achieved by adding 300 µL methanol containing 5 mM ammonium acetate. The extracts were obtained by centrifugation into the lower 96-deep well plate, followed by a dilution step with kit MS running solvent. Mass spectrometric analysis was performed on an API4000 Qtrap® tandem mass spectrometry instrument (Applied Biosystems/MDS Analytical Technologies, Foster City, Calif.) equipped with a solvent delivery system. The samples were delivered to the mass spectrometer by a LC method followed by a direct injection (DI) method. The Biocrates MetIQ software was used to control the entire assay workflow, from sample registration to automated calculation of metabolite concentrations to the export of data into other data analysis programs. A targeted profiling scheme was used to quantitatively screen for known small molecule metabolites using multiple reaction monitoring, neutral loss and precursor ion scans.

The data were log normalized. Principal component analysis is a multivariate technique and was used to find the two or three most useful metabolites (principal components) for distinguishing the two patient groups of interest. The first principal component is the single most discriminating metabolite while the second most discriminating metabolite is labeled the second principal component and so on.

Partial least squares discriminant analysis (PLS-DA) rotates around the different principal components to find the optimal combination for discriminating the case from the control group. Permutation analysis uses random re-sampling of case and controls to determine the probability that the observed and control groups is the result of chance. A total of 2000 re-samplings were performed. A p-value which represents the probability of a chance finding is generated. A variable importance in projection (VIP) plot (19) is a visual representation of the significance or importance of the particular metabolite in discriminating the groups of interest. The higher the VIP score, the more useful the metabolite for distinguishing normal from the affected group.

Statistical Analysis

All data were analyzed using software (Rand MetaboAnalyst). Univariate analysis of continuous data was conducted using Wilcoxon-Mann-Whitney test and categorical data were analyzed using Pearson Chi-Square and Fisher exact tests. Multivariate analyses were conducted using stepwise binary logistic regression with selected features using Lasso algorithm. Independent samples t-test, chi-square and Fisher exact tests were performed. A significance level of $P<0.05$ was used to define statistical significance.

Three different sets of analyses were performed. Metabolites were analyzed by themselves and also with addition of demographic such as, ethnicity, BMI, parity and an ultrasound marker namely CRL. Finally metabolites with Nuchal translucency (NT) were evaluated. It should be pointed out the Crown Rump Length (CRL) ultrasound measurement of the fetus is the most precise measure of gestational age and therefore used to assess whether first trimester gestational age affected maternal serum level of the metabolites.

For each metabolite, data normalization is critical to creating a normal or Gaussian distribution. Normalization allows conventional statistical tests to be performed, and it simplifies data interpretation. In this study we used log-transformed metabolite values, as noted previously.

Metabolite concentrations in CHD versus controls were compared. Stepwise logistic regression analyses were performed with CHD as the dependent variable and metabolites as the independent or determinant variable in order to develop a predictive algorithm for CHD detection. Metabolites with significant correlation with CHD status on univariate analysis were initially entered into the regression model development. Other variables including NT, fetal Crown Rump Length (CRL) and maternal demographics and medical status were combined with metabolite concentrations and run in the regression analyses. Finally, regression analyses including NT and the preceding metabolomic and maternal markers were performed for the prediction of CHD. Based on these analyses, several different regression equations for predicting the individual risk of CHD were developed. Individual risk or probability of CHD was calculated for each patient in the study. A series of paired sensitivity and FPR (1-specificity) values at different risk thresholds were calculated. A receiver operator characteristic (ROC) curve is plotted with sensitivity values on the Y-axis and the corresponding FPR (1-specificity) on the X-axis. The area under the ROC curve (AUC) indicates the accuracy of a test for correctly distinguishing a disorder such as CHD cases from normal (control). An AUC=1.0 indicates a perfect discriminating test. The 95% CI and p-values for the AUC curves were calculated. Permutation testing was also performed to determine the probability that the observed AUC obtained was due to chance.

Using direct injection mass spectrometry with LC-MS/MS (DI-MS) and NMR metabolomic platforms, numerous metabolites were identified in maternal serum that distinguished chromosomally normal versus first trimester CHD cases. The principal metabolite group identified was the acylcarnitines. This chemical group represents intermediates involved in the transport and metabolism of fatty acids in the mitochondria. In addition we demonstrated that the combination of a limited number of metabolites by themselves, e.g. hydroxypropionylcarnitine, glutaconylcarnitine and hydroxytetradecenoylcarnitine appeared to be highly accurate predictors of CHD status. The sensitivity of this combination of metabolites was 92% at a specificity threshold of 93.2%. These values were highly statistically significant.

When metabolites identified by the NMR platform alone were analyzed, only limited diagnostic accuracy was achieved. The combination of acetone and ethanol had a 67.9% sensitivity at 67.8% specificity. Though modest, these values were again statistically significant.

Nuchal translucency measurements are an important feature of first trimester ultrasound for aneuploidy risk determination. Several studies have confirmed a modest correlation between NT measurements in the first trimester and the risk of CHD. Higher NT measurements are said to correlate with increased CHD risk even in chromosomally normal fetuses. We therefore also looked at the combination of metabolite markers with NT measurement for the detection of CHD. While it was found to be a statistically significant predictor of CHD by itself, overall, there was no additional benefit of adding NT measurements to the metabolite markers. There was an approximately 4% increase in sensitivity and specificity when NT measurement was added to the combination of acetone and ethanol, this increase was not statistically significant however.

EXAMPLES

Study Design:

Mass spectrometry and NMR based metabolomic analyses were performed between 11 weeks and 13 weeks 6 days gestation on maternal serum. A total of 27 CHD cases and 59 controls were compared. There were no known or suspected chromosomal or syndromic abnormalities indicated.

The objectives of the current study are twofold. First, to determine whether there are significant differences in the first-trimester maternal metabolomic profile in pregnancies with a chromosomally normal fetus compared to those affected with a CHD. Secondly, to evaluate metabolite biomarker algorithms that might be useful for the first-trimester prediction of fetal CHD using maternal serum.

Methods:

This study is part of an ongoing prospective study for the first-trimester detection and prediction of fetal and maternal disorders. The details of specimen collection has been extensively described. (Bahado-Singh R O, et al. Metabolomics and first-trimester prediction of early-onset preeclampsia. J Matern Fetal Neonatal Med 2012; 10:1840-7; Bahado-Singh R O, et al. Metabolomic analysis for first-trimester Down Syndrome Prediction. Am J Obstet Gyencol 2013; 208; 371.e1-8.) The patients were prospectively recruited from an average risk population in Britain between 2003-2009. IRB approval was obtained through the institutional review board of King's College Hospital, London, England. Each recruited patient signed a written consent. Crown Rump Length (CRL) was used to estimate gestational age. Routine first-trimester screening for aneuploidy is the current standard of care. Maternal demographic and clinical data was obtained along with serum for PAPP-A and free B-hCG. Nuchal translucency measurement was measured for aneuploidy risk estimation. Karyotype and or newborn exams were performed to assess chromosomal status. CHD status was determined by prenatal imaging and or postnatal imaging and based on physical exam in the normal cases.

Results:

A total of 171 metabolites were evaluated. We identified 118 metabolites that demonstrated significant differences in maternal first-trimester serum in CHD versus normal cases. There was significant disturbance in acylcarnitine levels in CHD pregnancies. Predictive algorithms were developed for CHD detection. High sensitivity (95% CI)=0.97 (0.92, 1.00) and specificity (95% CI)=0.89 (0.78, 1.00) for CHD detection was achieved AUC (95% CI)=99.2 (0.973, 1.0).

There were 27 cases of CHD and 59 normal controls in which metabolomic analysis was able to be completed. Neither CHD or control fetuses had any known or suspected chromosomal or syndromic abnormalities. Table 1 gives the breakdown of the different types of CHD. Table 2 compares maternal pregnancy and other demographic characteristics between study and control groups. There were no significant difference observed. A total of 133 metabolites were identified and analyzed using DI-MS-direct flow injection mass spectrometry metabolomic platform. For NMR analysis a total of 38 metabolites were analyzed.

TABLE 1

| Types of CHD Cases |
| --- |
| AVSD/DORV |
| AVSD/DORV/PA |
| DORV/PS |
| DORV/PS |
| DORV/TOF |
| DORV/TOF |
| DORV/PA |
| TGA (3 cases) |
| TGA - corrected/VSD |
| TGA/PS |
| TOF (10 cases) |
| TOF/MS |
| TOF/PA (5 cases) |
| AVSD—Atrioventricular Septal Defect |
| DORV—Double Outlet Right Ventricle |
| MS—Mitral Stenosis |
| PA—Pulmonary Atresia |
| PS—Pulmonary Valve Stenosis |
| TGA—Transposition of the Great Artery |
| TOP—Tetralogy of Fallot |

TABLE 2

Maternal Demographic and medical characteristics:
Comparison of CHD and Control Groups

| Parameter | CHD | Control | P value |
|---|---|---|---|
| N | 28 | 59 | |
| Mean age, mean (SD)[a] | 29.2 (6.5) | 30.0 (5.2) | ns |
| Ethnicity, n (%)[b] | | | |
| Caucasian | 23 (82.1) | 47 (79.7) | ns |
| African American | 3 (10.7) | 10 (16.9) | |
| Asian/Other | 2 (7.1) | 2 (3.4) | |
| Nulliparous, n (%)[c] | | | ns |
| Multiparous | 12 (42.9) | 23 (39.0) | |
| Nulliparous | 16 (57.1) | 36 (61.0) | |
| BMI, mean (SD)[a] | 24.1 (4.2) | 24.4 (3.5) | ns |
| GA-CRL (weeks), mean (SD)[a] | 12.7 (0.7) | 12.7 (0.6) | ns |

CHD: congenital heart defect
ns: not significant
[a]Independent sampes t test
[b]X² test
[c]Fisher exact test
GA-CRL—gestational age in weeks based on crown rump length Using a DI-MS and NMR metabolomic analysis a total of 118 metabolites, were found to have significant concentration differences in maternal serum in CHD versus normal control cases on paired comparisons. The mean (SD) concentrations, T-test statistic and P-values for each metabolites along with fold change and direction of change in CHD cases relative to controls are provided in Table 3 for DI-MS analysis.

TABLE 3

Univariate Analysis for DI-MS: CHD vs. Control

| Metabolite (Biochemical Name) | Mean (SD) CHD | Mean (SD) Control | Fold Change | CHD/Control | p-value [a] |
|---|---|---|---|---|---|
| Number of cases | 27 | 59 | — | — | — |
| C0 (Carnitine) | 16.8 (14.32) | 24.41 (5.44) | −1.45 | Down | 0.0168 |
| C2 (Acetylcarnitine) | 2.5 (2.29) | 4.42 (1.79) | −1.77 | Down | 0.0008 |
| C3 (Propionylcarnitine) | 0.21 (0.18) | 0.3 (0.08) | −1.45 | Down | 0.0177 |
| C3:1 (Propenoylcarnitine) | 0.03 (0.02) | 0.03 (0.01) | −1.26 | Down | 0.0363 |
| C3—OH (Hydroxypropionylcarnitine) | 0.09 (0.06) | 0.18 (0.03) | −2 | Down | 0.0000 |
| C4 (Butyrylcarnitine) | 0.14 (0.12) | 0.22 (0.07) | −1.57 | Down | 0.0025 |
| C4:1 (Butenylcarnitine) | 0.03 (0.01) | 0.03 (0.01) | −1.23 | Down | 0.0641[NS] |
| C5 (Valerylcarnitine) | 0.08 (0.07) | 0.12 (0.02) | −1.39 | Down | 0.0070 |
| C5-M-DC (Methylglutarylcarnitine) | 0.05 (0.03) | 0.11 (0.04) | −2.29 | Down | 0.0000 |
| C5—OH(C3-DC-M) (Hydroxyvalerylcarnitine (Methylmalonylcarnitine)) | 0.06 (0.05) | 0.17 (0.07) | −2.88 | Down | 0.0000 |
| C5:1 (Tiglylcarnitine) | 0.03 (0.02) | 0.04 (0.01) | −1.13 | Down | 0.0553[NS] |
| C5:1-DC (Glutaconylcarnitine) | 0.07 (0.14) | 0.03 (0) | 2.76 | Up | 0.0130 |
| C6:1 (Hexenoylcarnitine) | 0.02 (0.01) | 0.03 (0) | −1.22 | Down | 0.0050 |
| C7-DC (Pimelylcarnitine) | 0.04 (0.03) | 0.03 (0.01) | 1.13 | Up | 0.1685[NS] |
| C8 (Octanoylcarnitine) | 0.09 (0.04) | 0.13 (0.05) | −1.38 | Down | 0.0018 |
| C9 (Nonaylcarnitine) | 0.04 (0.02) | 0.06 (0.02) | −1.67 | Down | 0.0000 |
| C10 (Decanoylcarnitine) | 0.13 (0.07) | 0.24 (0.11) | −1.93 | Down | 0.0000 |
| C10:1 (Decenoylcarnitine) | 0.2 (0.07) | 0.23 (0.05) | −1.13 | Down | 0.0045 |
| C10:2 (Decadienylcarnitine) | 0.03 (0.02) | 0.05 (0.02) | −1.57 | Down | 0.0001 |
| C12 (Dodecanoylcarnitine) | 0.04 (0.02) | 0.07 (0.02) | −1.45 | Down | 0.0003 |
| C12:1 (Dodecenoylcarnitine) | 0.24 (0.08) | 0.24 (0.04) | −1 | Down | 0.5894[NS] |
| C14 (Tetradecanoylcarnitine) | 0.03 (0.01) | 0.04 (0.01) | −1.19 | Down | 0.0003 |
| C14:1 (Tetradecenoylcarnitine) | 0.1 (0.08) | 0.2 (0.04) | −1.95 | Down | 0.0000 |
| C14:1—OH (Hydroxytetradecenoylcarnitine) | 0.01 (0.01) | 0.01 (0) | −1.04 | Down | 0.1545[NS] |
| C14:2 (Tetradecadienylcarnitine) | 0.01 (0.01) | 0.02 (0.01) | −1.6 | Down | 0.0001 |
| C14:2—OH (Hydroxytetradecadienylcarnitine) | 0.01 (0.01) | 0.01 (0) | −1.2 | Down | 0.0039 |
| C16 (Hexadecanoylcarnitine) | 0.05 (0.04) | 0.08 (0.02) | −1.67 | Down | 0.0000 |
| C16:2 (Hexadecadienylcarnitine) | 0.01 (0.01) | 0.01 (0) | −1.21 | Down | 0.0068 |
| C18 (Octadecanoylcarnitine) | 0.03 (0.02) | 0.04 (0.01) | −1.44 | Down | 0.0005 |
| C18:1 (Octadecenoylcarnitine) | 0.05 (0.04) | 0.08 (0.04) | −1.75 | Down | 0.0000 |
| C18:2 (Octadecadienylcarnitine) | 0.02 (0.02) | 0.03 (0.01) | −1.54 | Down | 0.0011 |
| lysoPC a C16:0 (lysoPhosphatidylcholine acyl C16:0) | 72.19 (66.13) | 142.06 (39.64) | −1.97 | Down | 0.0000 |
| lysoPC a C16:1 (lysoPhosphatidylcholine acyl C16:1) | 1.86 (1.86) | 2.68 (1.01) | −1.45 | Down | 0.0155 |
| lysoPC a C17:0 (lysoPhosphatidylcholine acyl C17:0) | 1.88 (2) | 2.64 (0.81) | −1.4 | Down | 0.0044 |
| lysoPC a C18:0 (lysoPhosphatidylcholine acyl C18:0) | 19.32 (17.98) | 36.49 (11.67) | −1.89 | Down | 0.0001 |
| lysoPC a C18:1 (lysoPhosphatidylcholine acyl C18:1) | 13.38 (12.74) | 27.95 (9.47) | −2.09 | Down | 0.0000 |

TABLE 3-continued

Univariate Analysis for DI-MS: CHD vs. Control

| Metabolite (Biochemical Name) | Mean (SD) CHD | Mean (SD) Control | Fold Change | CHD/Control | p-value [a] |
|---|---|---|---|---|---|
| lysoPC a C18:2 (lysoPhosphatidylcholine acyl C18:2) | 17.58 (17.13) | 36.34 (14.31) | −2.07 | Down | 0.0000 |
| lysoPC a C20:3 (lysoPhosphatidylcholine acyl C20:3) | 1.64 (1.55) | 2.74 (1.13) | −1.67 | Down | 0.0011 |
| lysoPC a C20:4 (lysoPhosphatidylcholine acyl C20:4) | 4.22 (3.72) | 7.99 (2.26) | −1.89 | Down | 0.0000 |
| lysoPC a C26:0 (lysoPhosphatidylcholine acyl C26:0) | 1.04 (1.05) | 0.73 (0.23) | 1.42 | Up | 1.0000 |
| lysoPC a C28:0 (lysoPhosphatidylcholine acyl C28:0) | 0.94 (1.03) | 0.75 (0.2) | 1.26 | Up | 0.4399 |
| lysoPC a C28:1 (lysoPhosphatidylcholine acyl C28:1) | 0.83 (0.79) | 0.83 (0.2) | −1.01 | Down | 0.4399 |
| PC aa C24:0 (Phosphatidylcholine diacyl C24:0) | 0.24 (0.25) | 0.16 (0.04) | 1.48 | Up | 0.7517 |
| PC aa C26:0 (Phosphatidylcholine diacyl C26:0) | 1.46 (0.88) | 1.21 (0.24) | 1.2 | Up | 0.5766 |
| PC aa C28:1 (Phosphatidylcholine diacyl C28:1) | 2.3 (1.98) | 3.44 (1.12) | −1.5 | Down | 0.0168 |
| PC aa C30:0 (Phosphatidylcholine diacyl C30:0) | 3.57 (3.29) | 6.08 (2.74) | −1.71 | Down | 0.0015 |
| PC aa C30:2 (Phosphatidylcholine diacyl C30:2) | 0.27 (0.34) | 0.59 (0.19) | −2.17 | Down | 0.0000 |
| PC aa C32:0 (Phosphatidylcholine diacyl C32:0) | 11.83 (10.25) | 21.47 (6.56) | −1.81 | Down | 0.0003 |
| PC aa C32:1 (Phosphatidylcholine diacyl C32:1) | 12.4 (12.89) | 23.35 (12.85) | −1.88 | Down | 0.0003 |
| PC aa C32:2 (Phosphatidylcholine diacyl C32:2) | 3.4 (3.23) | 6.59 (2.65) | −1.94 | Down | 0.0001 |
| PC aa C32:3 (Phosphatidylcholine diacyl C32:3) | 0.53 (0.47) | 0.88 (0.22) | −1.68 | Down | 0.0014 |
| PC aa C34:1 (Phosphatidylcholine diacyl C34:1) | 168.65 (151.58) | 316.44 (96.26) | −1.88 | Down | 0.0001 |
| PC aa C34:2 (Phosphatidylcholine diacyl C34:2) | 284.99 (253.25) | 512.41 (109.17) | −1.8 | Down | 0.0002 |
| PC aa C34:3 (Phosphatidylcholine diacyl C34:3) | 14.69 (13.19) | 26.71 (10.79) | −1.82 | Down | 0.0006 |
| PC aa C34:4 (Phosphatidylcholine diacyl C34:4) | 1.58 (1.41) | 2.93 (1.23) | −1.85 | Down | 0.0003 |
| PC aa C36:0 (Phosphatidylcholine diacyl C36:0) | 2.59 (2.32) | 3.38 (1.03) | −1.3 | Down | 0.0786 |
| PC aa C36:1 (Phosphatidylcholine diacyl C36:1) | 34.65 (31.86) | 65.28 (21.91) | −1.88 | Down | 0.0000 |
| PC aa C36:2 (Phosphatidylcholine diacyl C36:2) | 155.67 (140.71) | 279.02 (74.52) | −1.79 | Down | 0.0001 |
| PC aa C36:3 (Phosphatidylcholine diacyl C36:3) | 106.65 (95.96) | 188.8 (66.71) | −1.77 | Down | 0.0009 |
| PC aa C36:4 (Phosphatidylcholine diacyl C36:4) | 139.13 (121.52) | 260.54 (70.1) | −1.87 | Down | 0.0000 |
| PC aa C36:5 (Phosphatidylcholine diacyl C36:5) | 20.63 (20.91) | 42.04 (23.1) | −2.04 | Down | 0.0001 |
| PC aa C36:6 (Phosphatidylcholine diacyl C36:6) | 1.21 (1.14) | 2.13 (0.93) | −1.77 | Down | 0.0015 |
| PC aa C38:0 (Phosphatidylcholine diacyl C38:0) | 3.03 (2.75) | 5.09 (1.56) | −1.68 | Down | 0.0013 |
| PC aa C38:1 (Phosphatidylcholine diacyl C38:1) | 1.03 (1.27) | 1.46 (0.58) | −1.42 | Down | 0.0026 |
| PC aa C38:3 (Phosphatidylcholine diacyl C38:3) | 39.35 (35.4) | 67.85 (22.4) | −1.72 | Down | 0.0015 |
| PC aa C38:4 (Phosphatidylcholine diacyl C38:4) | 76.61 (64.78) | 141.13 (37.69) | −1.84 | Down | 0.0001 |
| PC aa C38:5 (Phosphatidylcholine diacyl C38:5) | 40.45 (34.59) | 76.98 (21.93) | −1.9 | Down | 0.0001 |
| PC aa C38:6 (Phosphatidylcholine diacyl C38:6) | 90.57 (84.14) | 178.28 (54.43) | −1.97 | Down | 0.0000 |
| PC aa C40:1 (Phosphatidylcholine diacyl C40:1) | 0.59 (0.35) | 0.61 (0.15) | −1.03 | Down | 0.0255 |
| PC aa C40:2 (Phosphatidylcholine diacyl C40:2) | 0.42 (0.43) | 0.47 (0.18) | −1.13 | Down | 0.0541 |
| PC aa C40:3 (Phosphatidylcholine diacyl C40:3) | 0.63 (0.61) | 0.78 (0.25) | −1.25 | Down | 0.0529 |
| PC aa C40:4 (Phosphatidylcholine diacyl C40:4) | 2.91 (2.55) | 4.96 (1.74) | −1.71 | Down | 0.0017 |
| PC aa C40:5 (Phosphatidylcholine diacyl C40:5) | 7.89 (6.89) | 14.08 (4.56) | −1.78 | Down | 0.0005 |

TABLE 3-continued

Univariate Analysis for DI-MS: CHD vs. Control

| Metabolite (Biochemical Name) | Mean (SD) CHD | Control | Fold Change | CHD/Control | p-value [a] |
|---|---|---|---|---|---|
| PC aa C40:6 (Phosphatidylcholine diacyl C40:6) | 28.03 (25.52) | 54.48 (16.86) | −1.94 | Down | 0.0000 |
| PC aa C42:0 (Phosphatidylcholine diacyl C42:0) | 0.68 (0.59) | 1.24 (0.38) | −1.83 | Down | 0.0000 |
| PC aa C42:1 (Phosphatidylcholine diacyl C42:1) | 0.33 (0.3) | 0.55 (0.15) | −1.65 | Down | 0.0009 |
| PC aa C42:2 (Phosphatidylcholine diacyl C42:2) | 0.23 (0.23) | 0.32 (0.1) | −1.38 | Down | 0.0130 |
| PC aa C42:4 (Phosphatidylcholine diacyl C42:4) | 0.22 (0.21) | 0.29 (0.08) | −1.33 | Down | 0.0200 |
| PC aa C42:5 (Phosphatidylcholine diacyl C42:5) | 0.52 (0.47) | 0.81 (0.26) | −1.58 | Down | 0.0052 |
| PC aa C42:6 (Phosphatidylcholine diacyl C42:6) | 0.93 (0.45) | 1.15 (0.3) | −1.23 | Down | 0.0123 |
| PC ae C30:0 (Phosphatidylcholine acly-alkyl C30:0) | 0.55 (0.42) | 0.58 (0.22) | −1.07 | Down | 0.1341 |
| PC ae C30:1 (Phosphatidylcholine acly-alkyl C30:1) | 0.37 (0.35) | 0.3 (0.12) | 1.22 | Up | 0.9481 |
| PC ae C32:1 (Phosphatidylcholine acly-alkyl C32:1) | 2.23 (1.98) | 3.8 (1.1) | −1.7 | Down | 0.0009 |
| PC ae C32:2 (Phosphatidylcholine acly-alkyl C32:2) | 0.7 (0.63) | 1.05 (0.26) | −1.51 | Down | 0.0085 |
| PC ae C34:0 (Phosphatidylcholine acly-alkyl C34:0) | 1.24 (1.1) | 1.96 (0.68) | −1.58 | Down | 0.0045 |
| PC ae C34:1 (Phosphatidylcholine acly-alkyl C34:1) | 7.95 (7.13) | 14.62 (4.86) | −1.84 | Down | 0.0002 |
| PC ae C34:2 (Phosphatidylcholine acly-alkyl C34:2) | 9.03 (8.28) | 15.62 (5.11) | −1.73 | Down | 0.0004 |
| PC ae C34:3 (Phosphatidylcholine acly-alkyl C34:3) | 6.56 (6.11) | 11.14 (3.09) | −1.7 | Down | 0.0003 |
| PC ae C36:0 (Phosphatidylcholine acly-alkyl C36:0) | 1 (1.17) | 1.04 (0.31) | −1.04 | Down | 0.0195 |
| PC ae C36:1 (Phosphatidylcholine acly-alkyl C36:1) | 7.06 (6.48) | 11.33 (3.59) | −1.6 | Down | 0.0048 |
| PC ae C36:2 (Phosphatidylcholine acly-alkyl C36:2) | 12.11 (10.98) | 20.84 (6.54) | −1.72 | Down | 0.0004 |
| PC ae C36:3 (Phosphatidylcholine acly-alkyl C36:3) | 6.38 (5.93) | 11.03 (3.88) | −1.73 | Down | 0.0005 |
| PC ae C36:4 (Phosphatidylcholine acly-alkyl C36:4) | 12.7 (10.97) | 21.9 (6.57) | −1.72 | Down | 0.0008 |
| PC ae C36:5 (Phosphatidylcholine acly-alkyl C36:5) | 8.03 (6.96) | 14.27 (3.66) | −1.78 | Down | 0.0001 |
| PC ae C38:0 (Phosphatidylcholine acly-alkyl C38:0) | 2.41 (2.07) | 3.92 (1.3) | −1.63 | Down | 0.0034 |
| PC ae C38:1 (Phosphatidylcholine acly-alkyl C38:1) | 0.88 (1.24) | 0.88 (0.41) | −1 | Down | 0.0114 |
| PC ae C38:2 (Phosphatidylcholine acly-alkyl C38:2) | 1.95 (1.97) | 3.01 (0.98) | −1.55 | Down | 0.0013 |
| PC ae C38:3 (Phosphatidylcholine acly-alkyl C38:3) | 3.9 (3.58) | 6.05 (2.14) | −1.55 | Down | 0.0100 |
| PC ae C38:4 (Phosphatidylcholine acly-alkyl C38:4) | 9.65 (8.29) | 17.69 (5.25) | −1.83 | Down | 0.0001 |
| PC ae C38:5 (Phosphatidylcholine acly-alkyl C38:5) | 11.95 (10.36) | 22.83 (6.42) | −1.91 | Down | 0.0000 |
| PC ae C38:6 (Phosphatidylcholine acly-alkyl C38:6) | 6.04 (5.42) | 11.04 (3.14) | −1.83 | Down | 0.0002 |
| PC ae C40:1 (Phosphatidylcholine acly-alkyl C40:1) | 1.09 (1.02) | 1.76 (0.55) | −1.62 | Down | 0.0011 |
| PC ae C40:2 (Phosphatidylcholine acly-alkyl C40:2) | 1.68 (1.53) | 2.65 (0.75) | −1.57 | Down | 0.0062 |
| PC ae C40:3 (Phosphatidylcholine acly-alkyl C40:3) | 1.2 (1.17) | 1.7 (0.52) | −1.41 | Down | 0.0155 |
| PC ae C40:4 (Phosphatidylcholine acly-alkyl C40:4) | 1.89 (1.67) | 3.22 (1.01) | −1.71 | Down | 0.0017 |
| PC ae C40:5 (Phosphatidylcholine acly-alkyl C40:5) | 3.17 (2.8) | 5.61 (1.62) | −1.77 | Down | 0.0004 |
| PC ae C40:6 (Phosphatidylcholine acly-alkyl C40:6) | 4.85 (4.4) | 9.04 (2.63) | −1.87 | Down | 0.0000 |
| PC ae C42:0 (Phosphatidylcholine acly-alkyl C42:0) | 0.85 (0.45) | 1.07 (0.29) | −1.25 | Down | 0.0048 |
| PC ae C42:1 (Phosphatidylcholine acly-alkyl C42:1) | 0.39 (0.35) | 0.52 (0.16) | −1.34 | Down | 0.0237 |
| PC ae C42:2 (Phosphatidylcholine acly-alkyl C42:2) | 0.53 (0.51) | 0.86 (0.26) | −1.61 | Down | 0.0015 |

TABLE 3-continued

Univariate Analysis for DI-MS: CHD vs. Control

| Metabolite (Biochemical Name) | Mean (SD) CHD | Mean (SD) Control | Fold Change | CHD/Control | p-value [a] |
|---|---|---|---|---|---|
| PC ae C42:3 (Phosphatidylcholine acly-alkyl C42:3) | 0.85 (0.82) | 1.39 (0.47) | −1.63 | Down | 0.0019 |
| PC ae C42:4 (Phosphatidylcholine acly-alkyl C42:4) | 1.01 (0.96) | 1.68 (0.6) | −1.66 | Down | 0.0027 |
| PC ae C42:5 (Phosphatidylcholine acly-alkyl C42:5) | 2.29 (1.83) | 3.95 (1.26) | −1.72 | Down | 0.0002 |
| PC ae C44:3 (Phosphatidylcholine acly-alkyl C44:3) | 0.14 (0.13) | 0.2 (0.07) | −1.43 | Down | 0.0021 |
| PC ae C44:4 (Phosphatidylcholine acly-alkyl C44:4) | 0.46 (0.42) | 0.73 (0.29) | −1.58 | Down | 0.0020 |
| PC ae C44:5 (Phosphatidylcholine acly-alkyl C44:5) | 2.03 (1.79) | 3.72 (1.35) | −1.83 | Down | 0.0001 |
| PC ae C44:6 (Phosphatidylcholine acly-alkyl C44:6) | 1.39 (1.21) | 2.51 (0.74) | −1.81 | Down | 0.0001 |
| SM (OH) C14:1 (Hydroxysphingomyeline C14:1) | 4.8 (4.33) | 7.99 (2.01) | −1.67 | Down | 0.0009 |
| SM (OH) C16:1 (Hydroxysphingomyeline C16:1) | 2.66 (2.28) | 4.44 (0.92) | −1.67 | Down | 0.0012 |
| SM (OH) C22:1 (Hydroxysphingomyeline C22:1) | 9.77 (8.46) | 16.71 (4.14) | −1.71 | Down | 0.0021 |
| SM (OH) C22:2 (Hydroxysphingomyeline C22:2) | 9.11 (7.71) | 15.52 (3.18) | −1.7 | Down | 0.0009 |
| SM (OH) C24:1 (Hydroxysphingomyeline C24:1) | 1.09 (0.95) | 1.74 (0.44) | −1.6 | Down | 0.0092 |
| SM C16:0 (Sphingomyeline C16:0) | 79.93 (68.46) | 141 (28.29) | −1.76 | Down | 0.0002 |
| SM C16:1 (Sphingomyeline C16:1) | 11.45 (10.08) | 20.32 (4.31) | −1.77 | Down | 0.0002 |
| SM C18:0 (Sphingomyeline C18:0) | 18.12 (15.99) | 31.1 (6.47) | −1.72 | Down | 0.0003 |
| SM C18:1 (Sphingomyeline C18:1) | 8.29 (7.21) | 14.7 (3.13) | −1.77 | Down | 0.0002 |
| SM C20:2 (Sphingomyeline C20:2) | 0.82 (0.83) | 1.71 (0.46) | −2.09 | Down | 0.0000 |
| SM C22:3 (Sphingomyeline C22:3) | 4.57 (5.46) | 13.34 (3.81) | −2.92 | Down | 0.0000 |
| SM C24:0 (Sphingomyeline C24:0) | 16.75 (14.33) | 29.46 (7.46) | −1.76 | Down | 0.0008 |
| SM C24:1 (Sphingomyeline C24:1) | 43.05 (37.37) | 79.01 (16.72) | −1.84 | Down | 0.0000 |
| SM C26:0 (Sphingomyeline C26:0) | 0.19 (0.21) | 0.25 (0.07) | −1.31 | Down | 0.0074 |
| SM C26:1 (Sphingomyeline C26:1) | 0.33 (0.29) | 0.54 (0.14) | −1.64 | Down | 0.0057 |
| H1 (Hexose) | 3183.4 (2827.17) | 5506.57 (1243.87) | −1.73 | Down | 0.0009 |

[a] Non-Parametric testing.

In Table 4, a similar comparison of metabolite concentrations was performed for only NMR based metabolomics. Significant differences were noted in five metabolites using the NMR platform.

TABLE 4

Univariate Analysis for NMR: CHD vs Control

| Metabolite | Mean (SD) CHD | Mean (SD) Control | Fold Change | CHD/Control | p-value [a] |
|---|---|---|---|---|---|
| Number of cases | 27 | 59 | — | — | — |
| 2-Hydroxybutyrate | 17.13 (7.48) | 16.69 (6.25) | 1.03 | Up | 0.8963 |
| 3-Hydroxybutyrate | 33.63 (42.57) | 30.15 (37.69) | 1.12 | Up | 0.4208 |
| Acetamide | 6.56 (3.47) | 7.78 (5.04) | −1.19 | Down | 0.5828 |
| Acetate | 25.69 (7.99) | 29.85 (8.26) | −1.16 | Down | 0.0207* |
| Acetoacetate | 14.33 (10.92) | 12.64 (8.21) | 1.13 | Up | 0.6822 |
| Acetone | 15 (4.34) | 18.46 (5.83) | −1.23 | Down | 0.0039* |
| Alanine | 284.62 (65.96) | 267.32 (53.39) | 1.06 | Up | 0.1440 |
| Betaine | 21.99 (7.84) | 20.05 (8.39) | 1.1 | Up | 0.2056 |
| Carnitine | 21.08 (4.88) | 19.98 (4.82) | 1.06 | Up | 0.1894 |
| Choline | 7.68 (3.02) | 7.49 (2.69) | 1.03 | Up | 0.8123 |

TABLE 4-continued

Univariate Analysis for NMR: CHD vs Control

| Metabolite | Mean (SD) CHD | Mean (SD) Control | Fold Change | CHD/Control | p-value [a] |
|---|---|---|---|---|---|
| Citrate | 59.29 (11.58) | 61.85 (13.38) | −1.04 | Down | 0.4510 |
| Creatine | 25.5 (11.41) | 23.84 (11.5) | 1.07 | Up | 0.3449 |
| Creatinine | 36.96 (8.1) | 35.54 (9.46) | 1.04 | Up | 0.1879 |
| Dimethyl sulfone | 5.06 (3.56) | 4.78 (2.73) | 1.06 | Up | 0.9703 |
| Ethanol | 46.68 (25.73) | 32.21 (16.46) | 1.45 | Up | 0.013* |
| Glucose | 3241.19 (898.95) | 3171.93 (754.22) | 1.02 | Up | 0.7376 |
| Glutamate | 52.21 (14.83) | 56.4 (12.69) | −1.08 | Down | 0.1147 |
| Glutamine | 311.3 (55.65) | 310.98 (52.92) | 1 | Up | 1.0000 |
| Glycerol | 124.62 (45.58) | 133.9 (34.38) | −1.07 | Down | 0.1614 |
| Glycine | 141.82 (37.97) | 135.06 (40.06) | 1.05 | Up | 0.2040 |
| Isobutyrate | 4.59 (1.89) | 4.65 (2.06) | −1.01 | Down | 0.9888 |
| Isoleucine | 43.24 (16.72) | 40.9 (11.7) | 1.06 | Up | 0.6652 |
| Lactate | 1236.89 (410.48) | 1270.97 (604.28) | −1.03 | Down | 0.7341 |
| Leucine | 73.74 (23.04) | 69.55 (16.39) | 1.06 | Up | 0.7028 |
| Lysine | 103.04 (27.01) | 97.44 (29.48) | 1.06 | Up | 0.2073 |
| Malonate | 11.84 (2.88) | 11.11 (3) | 1.07 | Up | 0.1754 |
| Methionine | 16.34 (4.74) | 15.3 (4.66) | 1.07 | Up | 0.2317 |
| Ornithine | 25.15 (7.57) | 22.37 (8.47) | 1.12 | Up | 0.1365 |
| Phenylalanine | 44.46 (12.81) | 43.9 (15.78) | 1.01 | Up | 0.5058 |
| Proline | 111.43 (37.73) | 106 (33.59) | 1.05 | Up | 0.5484 |
| Propylene glycol | 8.84 (2.78) | 8.25 (2.09) | 1.07 | Up | 0.4047 |
| Pyruvate | 63.92 (19.24) | 54.52 (25.5) | 1.17 | Up | 0.0155* |
| Serine | 75.47 (22.9) | 77.55 (23.11) | −1.03 | Down | 0.9370 |
| Succinate | 3.35 (1.78) | 3.31 (1.13) | 1.01 | Up | 0.5506 |
| Threonine | 112.57 (25.66) | 107.31 (26.21) | 1.05 | Up | 0.3449 |
| Tyrosine | 42.94 (11.38) | 45.63 (19.15) | −1.06 | Down | 0.9296 |
| Valine | 147.88 (37.36) | 143.24 (30.09) | 1.03 | Up | 0.5148 |
| -Methylhistidine | 26.93 (13.26) | 23.74 (15.16) | 1.13 | Up | 0.0185* |

Figure 2:
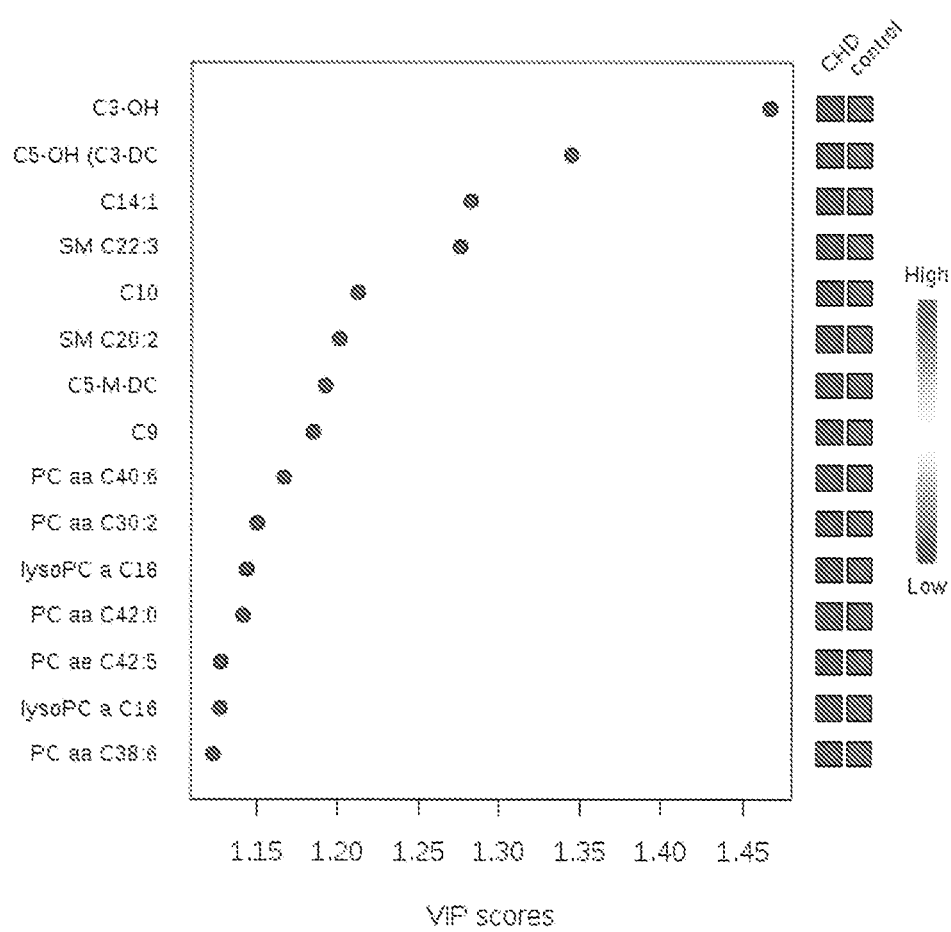
FIG. 2 depicts a VIP scores Plot, DI-MS Based Metabolites.

Using DI-MS data alone, PCA showed clustering of the control from the CHD specimens. This indicates that the two groups could be significantly distinguished based on a limited number (two) of metabolites. The most discriminating metabolite, PC1 or principal component 1, accounted for 84.0% of the observed separation between groups. The second metabolite PC2 accounted for 3.5% of the separation. Two-dimensional PLS-DA further confirmed the discrimination of the CHD from control groups that was achieved by these metabolites. In that PLS-DA plot, one metabolite accounted for 83.9% of the discrimination (PC1) while the second metabolite was responsible for 2.7% of the separation between groups. The 3-D PLS-DA plot (FIG. 1) of the DI-MS identified metabolites similarly demonstrated excellent separation of the two groups using three rather than two discriminating metabolites. VIP scores plot for the DI-MS based metabolites is shown in FIG. 2. The plot shows metabolites with VIP scores >1. The following three metabolites C3-OH, C5.OH(C3DC) and C14:1 appeared most predictive for CHD detection with DI-MS analysis.

Figure 3:
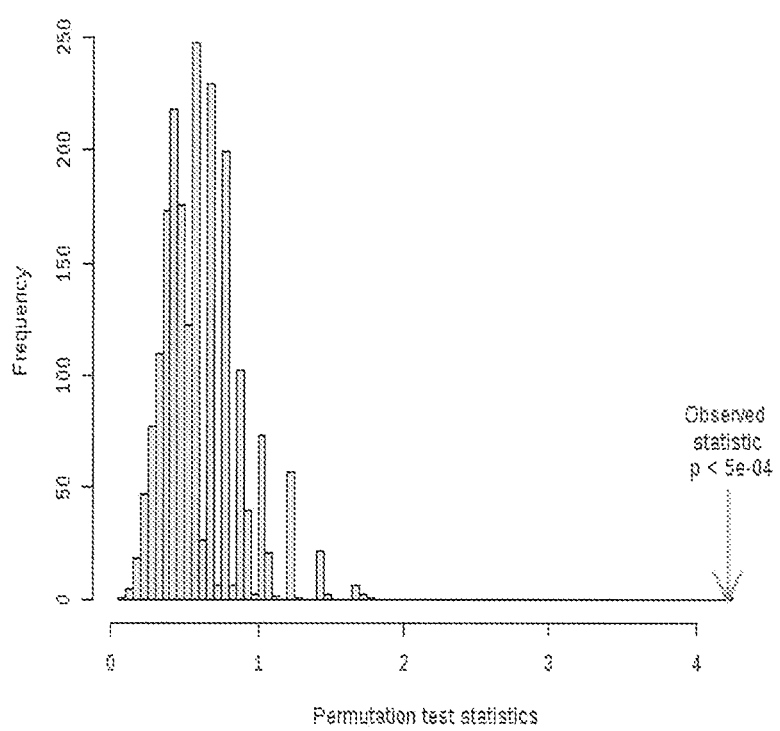
FIG. 3 depicts permutation testing for DI-MS only; Permutation Test (n=2000), P-value=0.0005.

Permutation testing using n=2000 re-samplings showed a highly statistically significant p value, <0.005, indicating that the observed separation between groups was unlikely to be due to chance (FIG. 3).

Figure 4:
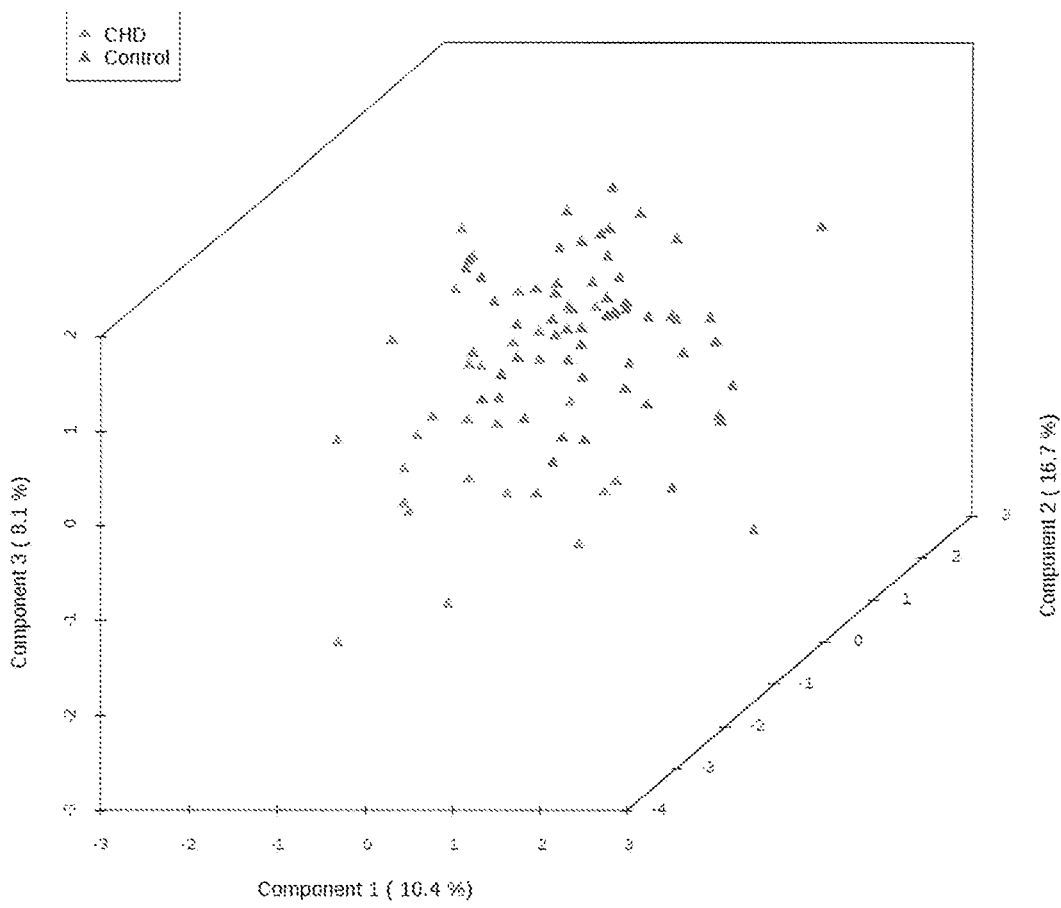
FIG. 4 depicts a 3-D PLS-DA plot using NMR only.
Figure 5:
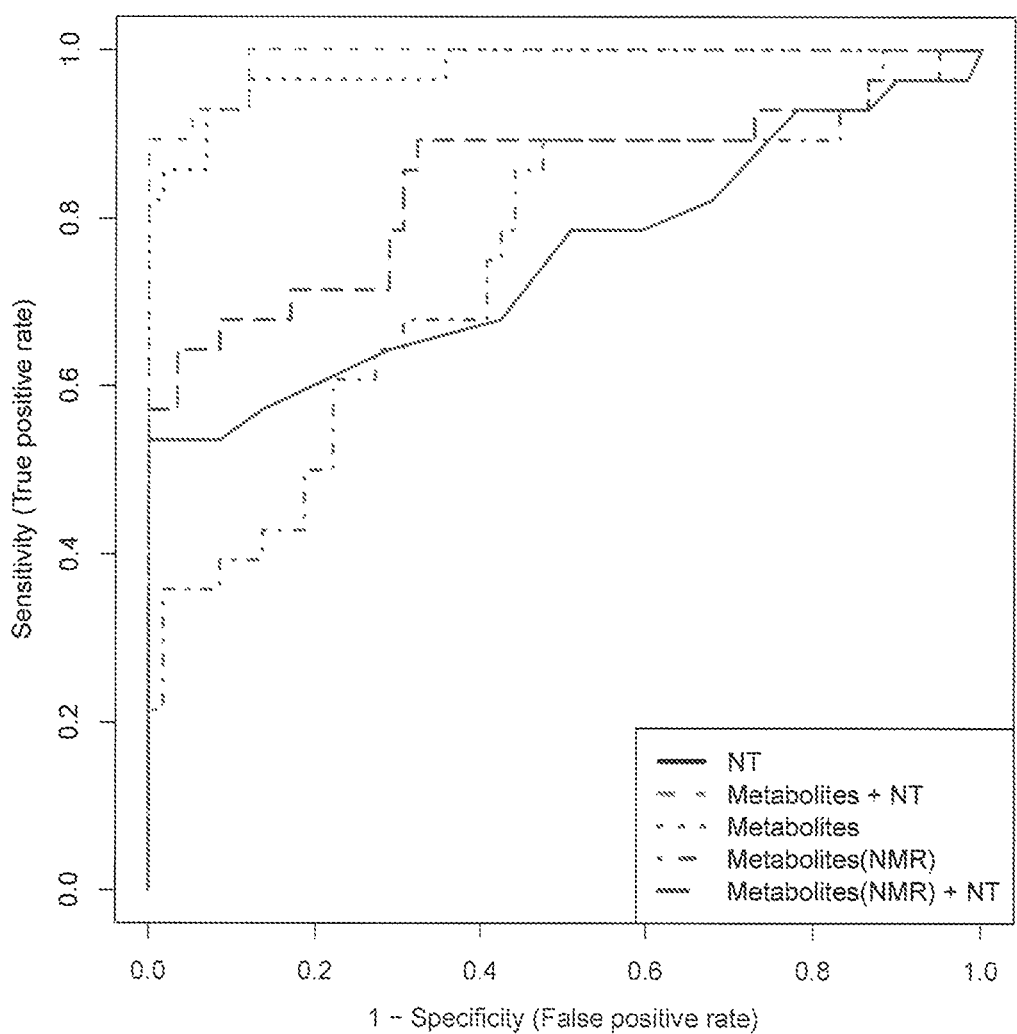
FIG. 5 depicts a ROC comparison of all logistic regression models produced in this study. NT: AUC=0.753, Metabolites (DI-MS and NMR)+NT: AUC=0.992, Metabolites (DI-MS and NMR): AUC=0.981, Metabolites (NMR)+NT: AUC=0.847, and Metabolites (NMR): AUC=0.749. NT, Nuchal Translucency; Metabolites: DI-MS and NMR, and three metabolites used in the model (Hydroxypropionylcarnitine, Glutaconylcarnitine, and Hydroxytetradecadienylcarnitine); Metabolites (NMR): Acetone, Ethanol.

A similar series of analyses were performed using metabolites detected based on the NMR platform. Some clustering of cases relative to controls was observed on PCA analysis; however the separation was not as marked as for the DI-MS analysis. Separation of CHD and controls were observed on 2-D PLS-DA analysis, but were improved when 3 rather than 2 principal components were used. See, 3D plot (FIG. 4). Permutation testing using 2000 re-samplings for the NMR analysis also yielded a low probability that the observed separation was due to chance, p=0.002. The corresponding VIP plot (FIG. 5) showed acetone, ethanol, acetate and pyruvate to be the 4 most discriminating metabolites using NMR analysis.

Using logistic regression analysis the individual probability of a fetus having CHD was calculated using 3 metabolites from the DI-MS based metabolomics results, namely C3-OH, C5:1-DC and C14:2-OH (Table 5). The logistic equations was represented by risk of CHD=f[−42.582− 12.039 log (C3-OH)+3.194 log (C5:1-DC)-4.050 log (C14:2-OH)], where f represents the logistic function. The table shows the contribution of each of these DI-MS based metabolites to the CHD prediction model. The ROC curve (FIG. 5) indicates that this metabolite combination was a highly significant predictor of CHD:AUC (95% CI)=0.981 (0.942, 0.999). The sensitivity (95% CI) and specificity (95% CI) of the algorithms were statistically significant: 0.98 (0.95, 1.00) and 0.82 (0.68, 0.96) respectively. Permutation testing for the optimal model was performed using 2000 random samples and indicated a low probability that the diagnostic accuracy represented by the area under the ROC curve was due to chance, p<0.0005. The sensitivities at different false positive thresholds for the algorithm or NMR-based analysis only are shown in Table 6. On a further analysis CRL, ethnicity, BMI or parity did not contribute significantly to CHD prediction using metabolites.

TABLE 5

Logistic Regression Based Optimal Model for CHD Detection: DI-MS Metabolites Only

| | Estimates (B) | Std. Emer | Z-Value | PR (>121) |
|---|---|---|---|---|
| (Intercept) | −42.582 | 18.604 | −2.289 | 0.022 |
| C3—OH | −12.039 | 5.227 | −2.303 | 0.021 |

TABLE 5-continued

Logistic Regression Based Optimal Model
for CHD Detection: DI-MS Metabolites Only

|         | Estimates (B) | Std. Emer | Z-Value | PR (>121) |
|---------|---------------|-----------|---------|-----------|
| C5:1-DC | 3.194         | 1.075     | 2.972   | 0.003     |
| C14:2—OH | −4.050       | 1.710     | −2.369  | 0.017     |

Null deviance: 109.32 or 86 degrees of freedom
Residual deviance: 27.67 or 83 degrees of freedom
CHD = f[42.582 − 12.039 log (C3—OH) + 3.194 log (C5:1-DC) − 4.050 log (c14.2-OH)]
represents the equation for the prediction of CHD

TABLE 6

NMR only prediction of CHD

| Metabolites/markers | AUC (95% CI)         | Sensitivity (%) | Specificity (%) | P-value |
|---------------------|----------------------|-----------------|-----------------|---------|
| Metabolites* only   | 0.749 (0.628, 0.854) | 67.9            | 67.8            | 0.002   |
| Metabolites + NT    | 0.847 (0.729, 0.937) | 71.4            | 71.2            | <0.001  |

Metabolites* - acetone and ethanol
P-value represents the permutation testing p-value We also looked at the performance of the algorithm using the NMR only platform and also these metabolites combined with NT (Table 6). NT contributed only modestly and did not significantly improve performance over NMR only metabolites.

Using NT measurement only, the following predictive equation for CHD risk estimation was developed: CHD risk=f(−4.821+1.873 NT): where NT was the nuchal translucency measurement. The AUC (95% CI) for this algorithm was 0.753 (0.616, 0.867). Sensitivity (95% CI) was 0.97 (0.92, 1.00) and for specificity this was 0.54 (0.351, 0.72). The positive likelihood ratio was 2.08 with an accuracy of 0.83.

Analyses were also performed using both NMR and DI-MS metabolites, and NT ultrasound measurement for a CHD prediction. That prediction model was represented by the logistic equation CHD=f[−58.0591+2.1678NT−14.2494 log (C3-0H)+2.9807 log (C5:1-DC) 4.6776 log (C14:2-OH). This combination was a highly statistically significant predictor of CHD with AUC (95% CI): 0.992 (0.973, 1.0). The sensitivity (95% CI) of the model was 0.97 (0.92, 1.00) and the specificity (95% CI) of this model was also statistically significant: 0.89 (0.78, 1.00). The overall accuracy based on combining all metabolites and NT was 0.94 for discriminating the two groups was 0.94 with a false discovery rate of 0.05%. Permutation testing using 2000 resamples confirmed a low probability that the observed area under the ROC curve was due to chance, p<0.0005. This did not however represent a significant improvement over the metabolites only algorithm as shown in table 7.

TABLE 7

CHD Prediction based on limited metabolite
combinations: DI-MS based Metabolites

| Metabolites/markers | AUC (95% CI)         | Sensitivity (%) | Specificity (%) | P-value |
|---------------------|----------------------|-----------------|-----------------|---------|
| Metabolites* only   | 0.981 (0.942, 0.999) | 92.9            | 93.2            | <0.001  |
| Metabolites + NT    | 0.992 (0.973, 1.0)   | 92.9            | 93.2            | <0.001  |

TABLE 7-continued

CHD Prediction based on limited metabolite
combinations: DI-MS based Metabolites

| Metabolites/markers | AUC (95% CI)         | Sensitivity (%) | Specificity (%) | P-value |
|---------------------|----------------------|-----------------|-----------------|---------|
| NT only             | 0.753 (0.616, 0.867) | 64.3            | 71.2            | 0.001   |

*Metabolites—Hydroxypropionylcarnitine, Glutaconylcarnitine, Hydroxytetradecadienyl-carntine
NT—nuchal translucency
P-value—permutations testing p-value

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

What is claimed is:

1. A method of predicting a congenital heart defect in a patient, the method comprising obtaining a biological sample from a patient and assaying acylcarnitine levels in the biological sample using nuclear magnetic resonance and direct flow injection mass spectrometry, wherein the patient is an embryo, a fetus, a newborn, or a pediatric patient and wherein the acylcarnitine is one or more of C3-OH, C5-OH, C10, C5:1-DC, C14:1-OH, or C14:2-OH.

2. The method of claim 1, wherein the patient is an embryo or a fetus and the biological sample is obtained from a pregnant woman carrying the embryo or fetus.

3. The method of claim 2, wherein the biological sample is obtained from a pregnant woman during first trimester of pregnancy, second trimester of pregnancy, or third trimester of pregnancy.

4. The method of claim 1, wherein the biological sample is selected from the group consisting of saliva, urine, amniotic fluid, breath condensate, placental tissue, and blood.

5. The method of claim 4, wherein the blood is umbilical cord blood or maternal blood.

6. The method of claim 3, wherein the biological sample is selected from the group consisting of saliva, urine, amniotic fluid, breath condensate, blood, and placental tissue.

7. A method for predicting a congenital heart defect in an embryo or a fetus of a pregnant woman, the method comprising measuring acylcarnitine levels in a biological sample from the pregnant woman using nuclear magnetic resonance and mass spectrometry, wherein the acylcarnitine is one or more of C3-OH, C5-OH, C10, C5:1-DC, C14:1-OH, or C14:2-OH.

8. The method of claim 7, wherein the pregnant woman is in her first trimester of pregnancy, the second trimester of pregnancy, or the third trimester of pregnancy.

9. The method of claim 7, further comprising measuring the nuchal translucency of the fetus.

10. The method of claim 7, wherein the biological sample is selected from the group consisting of saliva, urine, amniotic fluid, breath condensate, placental tissue, and blood.

11. The method of claim 10, wherein the biological sample is blood.

12. A method for diagnosing a congenital heart defect in a patient, the method comprising measuring acylcarnitine levels in a biological sample from the patient using nuclear magnetic resonance and mass spectrometry, wherein the acylcarnitine is one or more of C3-OH, C5-OH, C10, C5:1-DC, C14:1-OH, or C14:2-OH, and wherein the patient is an embryo, a fetus, a newborn, or a pediatric patient.

13. The method of claim 12, wherein the biological sample is selected from the group consisting of saliva, urine, breath condensate, blood, and placental tissue.

14. The method of claim 7, wherein the mass spectrometry is direct flow injection mass spectrometry.

15. The method of claim 12, wherein the mass spectrometry is direct flow injection mass spectrometry.

* * * * *